United States Patent [19]
Warrin et al.

[11] Patent Number: 5,419,703
[45] Date of Patent: May 30, 1995

[54] METHOD OF SUBGINGIVAL SCALING AND LAVAGE

[75] Inventors: George E. Warrin, North Merrick; Rene J. Perdreaux, Brooklyn, both of N.Y.

[73] Assignee: Dentsply Research & Development Corp., Milford, Del.

[21] Appl. No.: 296,844

[22] Filed: Aug. 26, 1994

Related U.S. Application Data

[63] Continuation of Ser. No. 880,281, May 1, 1992, abandoned, which is a continuation of Ser. No. 157,814, Feb. 18, 1988, abandoned.

[51] Int. Cl.$^6$ ............... A61C 15/00; A61C 1/07
[52] U.S. Cl. ................... 433/216; 433/86
[58] Field of Search ............ 433/80, 81, 86, 119, 433/216; 601/162

[56] References Cited

U.S. PATENT DOCUMENTS

| | | | |
|---|---|---|---|
| Re. 30,536 | 3/1981 | Perdreaux, Jr. | 433/86 |
| 2,874,470 | 5/1954 | Richards | 32/58 |
| 3,077,415 | 6/1960 | Ayers | 106/75 |
| 3,368,280 | 2/1968 | Friedman et al. | 32/58 |
| 3,593,423 | 4/1969 | Jones et al. | 32/22 |
| 3,636,947 | 1/1972 | Balamuth | 128/66 |
| 3,693,613 | 9/1972 | Kelman | 128/24 A |
| 3,703,037 | 11/1972 | Robinson | 32/58 |
| 3,718,973 | 3/1973 | Slater et al. | 32/22 |
| 3,760,799 | 9/1973 | Crowson | 128/24 A |
| 3,807,048 | 4/1974 | Malmin | 32/40 R |
| 3,809,977 | 5/1974 | Balamuth et al. | 433/119 X |
| 3,863,628 | 2/1975 | Vit | 128/66 |
| 3,924,335 | 12/1975 | Balamuth et al. | 32/58 |
| 3,930,173 | 12/1975 | Banko | 310/26 |
| 4,012,842 | 3/1977 | Vit | 32/58 |
| 4,116,239 | 9/1978 | Ewen | 128/184 |
| 4,148,309 | 4/1979 | Reibel | 128/24 A |
| 4,162,576 | 7/1979 | Takemoto et al. | 32/40 R |
| 4,249,901 | 2/1981 | Wieser | 433/119 |
| 4,260,380 | 4/1981 | Nash | 433/119 |
| 4,276,880 | 7/1981 | Malmin | 128/221 |
| 4,283,175 | 8/1981 | Nash | 433/119 |
| 4,291,017 | 9/1981 | Beierle et al. | 424/52 |
| 4,295,827 | 10/1981 | Martin et al. | 433/81 |
| 4,330,278 | 5/1982 | Martin | 433/81 |
| 4,332,558 | 6/1982 | Lustig | 433/119 X |
| 4,370,131 | 1/1983 | Banko | 433/86 |
| 4,492,574 | 1/1985 | Warrin et al. | 433/81 |
| 4,505,676 | 3/1985 | Gonser | 433/119 |
| 4,592,728 | 6/1986 | Davis | 433/80 |
| 4,731,019 | 3/1988 | Martin | 433/119 |

FOREIGN PATENT DOCUMENTS

| | | | |
|---|---|---|---|
| 2364028 | 4/1978 | France . | |
| 2406437 | 5/1979 | France . | |
| 446818 | 7/1927 | Germany | 128/221 |
| 180356 | 5/1954 | Germany . | |
| 7002091 | 1/1970 | Germany . | |
| 2329728 | 1/1974 | Germany . | |
| 1469399 | 4/1977 | United Kingdom . | |
| 8704613 | 8/1987 | WIPO . | |

OTHER PUBLICATIONS

Pages taken from the Cavi-Jet 3 Instruction Manual. pp. 8-12.
A Method For Altering The Periodontal Pocket Environment From Anaerobic To Aerobic—Paul N. Baer—Periodontal Case Reports vol. 7 No. 1, 1985.
Dentsply/Equipment Division Instruction Manual front page and pp. 8-13.

*Primary Examiner*—Nicholas D. Lucchesi
*Attorney, Agent, or Firm*—Dale R. Lovercheck; Edward J. Hanson, Jr.

[57] ABSTRACT

An insert for use in an apparatus for scaling of teeth and lavage of the gingival sulcus is provided. The insert comprises a tip for scaling and delivery of lavage fluids, retaining means for retaining the scaling tip in the insert, and a path means for delivering irrigant for scaling or for lavage through the insert and to the end of the scaling tip. The scaling tip is shaped and dimensioned for scaling and lavage below the gumline in periodontal pockets. When a magnetostrictive insert is used, an outlet means is provided to remove stack cooling water from the insert so that stack cooling water does not enter a patient's mouth.

26 Claims, 5 Drawing Sheets

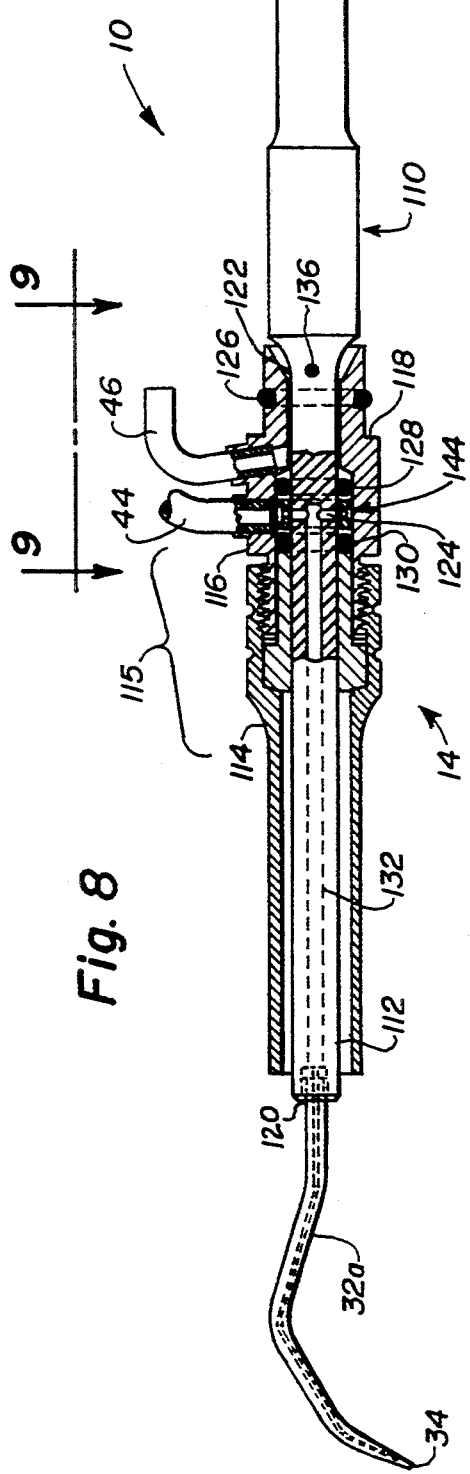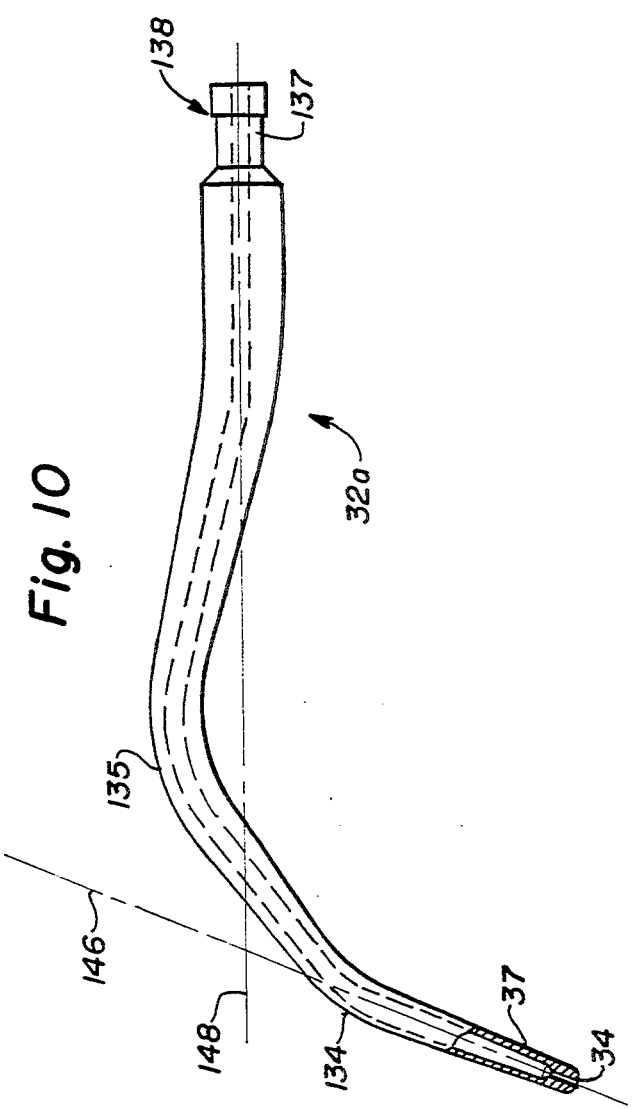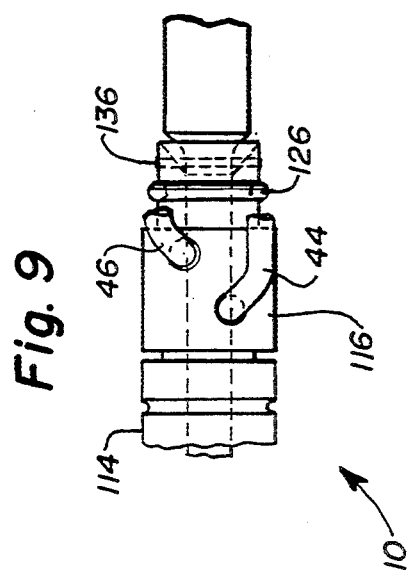

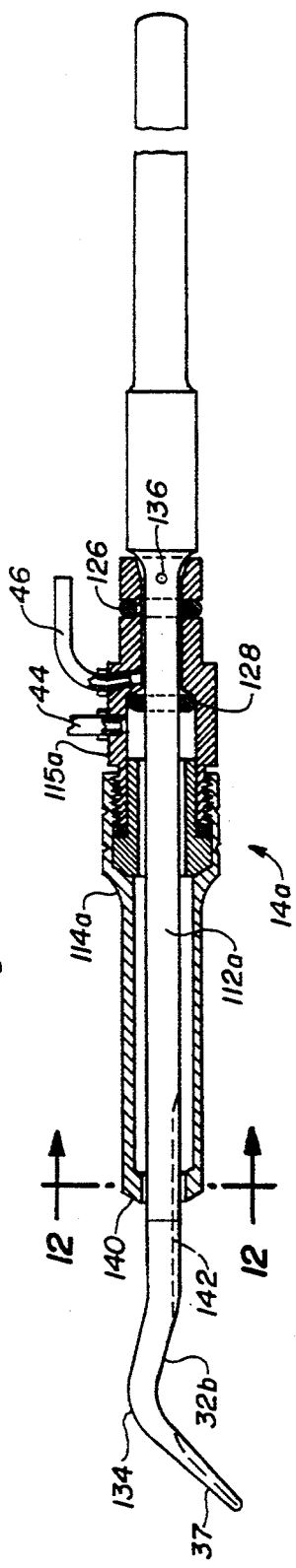

METHOD OF SUBGINGIVAL SCALING AND LAVAGE

This is a continuation of patent application Ser. No. 070/880,281, now abandoned, filed May 1, 1992 which is a continuation of patent application Ser. No. 07/157,814, filed Feb. 18, 1988, and now abandoned.

BACKGROUND OF THE INVENTION

The present invention relates to an insert for use in an apparatus for scaling of teeth, and for lavage of the gingival sulcus and other parts of the mouth requiring lavage. The apparatus is capable of providing scaling alone, lavage alone, or for providing both simultaneously.

It is known in the art that plaque and calculus harbor toxic and irritating components implicated in oral disease and that plaque and calculus can be removed from teeth by high frequency scaling. Many instruments are known in the art for that purpose. Prior art scaling instruments have been designed with scaling tips that are caused to vibrate at frequencies between about 6 and 50 KHZ using mechanical, magnetostrictive or piezoelectric energy. Scaling tips for the prior art devices are relatively large since they are used mainly to remove plaque and calculus from the exposed, relatively large, flat surfaces of teeth. With a few exceptions, prior art scaling tips are too large for scaling below the gum line in periodontal pockets, unless the pockets are surgically exposed.

Because heat is generated by the vibration of the stacks and scaling tips, most prior art scaling devices have a conduit that transports tap water to the handpiece and onto the scaling tip for cooling thereof. In magnetostrictive devices, for example, the tap water is first used to circulate around the transducer stack to cool the stack, and is then dispensed onto the scaling tip to cool the tip. In piezoelectric devices the cooling water is directed to the scaling tip only. The cooling water is thereafter dispensed into the patient's mouth during the scaling procedure to cleanse the operating field of debris.

It is also known in the art to provide instruments to oxygenate or irrigate periodontal pockets with oxygenated or oxygen producing chemicals. This is done because it has been found that anaerobic bacteria live in periodontal pockets, (it has been inferred that a causal relationship between the presence of anaerobic bacteria and periodontal disease exists) and anaerobic bacteria cannot live in the presence of oxygen. Similarly other antibacterial solutions may be prepared to facilitate removal of calculus, plaque and plaque components by irrigation. Such procedures are commonly known in the art as lavage.

It has been found that a conscientious program of keeping teeth clean of adhering calculus and plaque, and irrigating periodontal pockets with one or more suitable lavage irrigants may stop or even reverse the progression of periodontal disease.

In the past, however, to provide both procedures, two different apparatus were required. The practitioner, to provide adequate treatment, was faced with the expense and clutter of two independent sets of equipment, and the need to use both sets of equipment when using both procedures was time consuming and cumbersome.

It is the object of the present invention to overcome the problems with the prior art procedures and apparatus.

SUMMARY OF THE INVENTION

An insert for use in an apparatus used for scaling teeth and for therapeutic lavage is provided. The insert comprises a scaling tip, retaining means for retaining the scaling tip in the insert and a path means for delivering irrigant for scaling or for lavage through the insert to the end of the scaling tip. In one embodiment, the path means comprises an inlet for permitting flow of fluid into the retaining means and a bore through the scaling tip communicating with the inlet. In a second embodiment, a channel on the outside of the scaling tip directs fluid from the retaining means to the distal end of the scaling tip. In an embodiment in which the insert is used for ultrasonic scaling, and the insert comprises as a part thereof a magnetostrictive stack, the insert has an outlet for removing stack cooling water from around the stack so that the stack cooling water is not dispensed into the mouth of a patient. The scaling tip is shaped and dimensioned for scaling and lavage below the gumline in periodontal pockets. Inserts having specific shapes for use in deep periodontal pockets, and left and right bends for access for scaling between and under the roots of molars are also provided.

BRIEF DESCRIPTION OF THE DRAWINGS

FIG. 8 is an embodiment of the insert of the invention which uses end delivery of irrigant.

FIG. 9 is section 9—9 of FIG. 8 rotated 90°.

FIG. 10 illustrates a preferred shape of a scaling/lavage tip with a double bend.

FIG. 11 is an embodiment of an insert which has a tip design adapted to direct irrigant on the outside of the scaling tip.

FIG. 12 is an end view along line 12—12 of the embodiment of FIG. 11.

FIG. 13 illustrates a second preferred shape of a scaling/lavage tip with a gooseneck.

FIG. 14 illustrates a scaling tip for right molar root planing.

FIG. 15 is an end view along line 15—15 of the embodiment of FIG. 14.

DETAILED DESCRIPTION OF THE INVENTION

Figure 1:
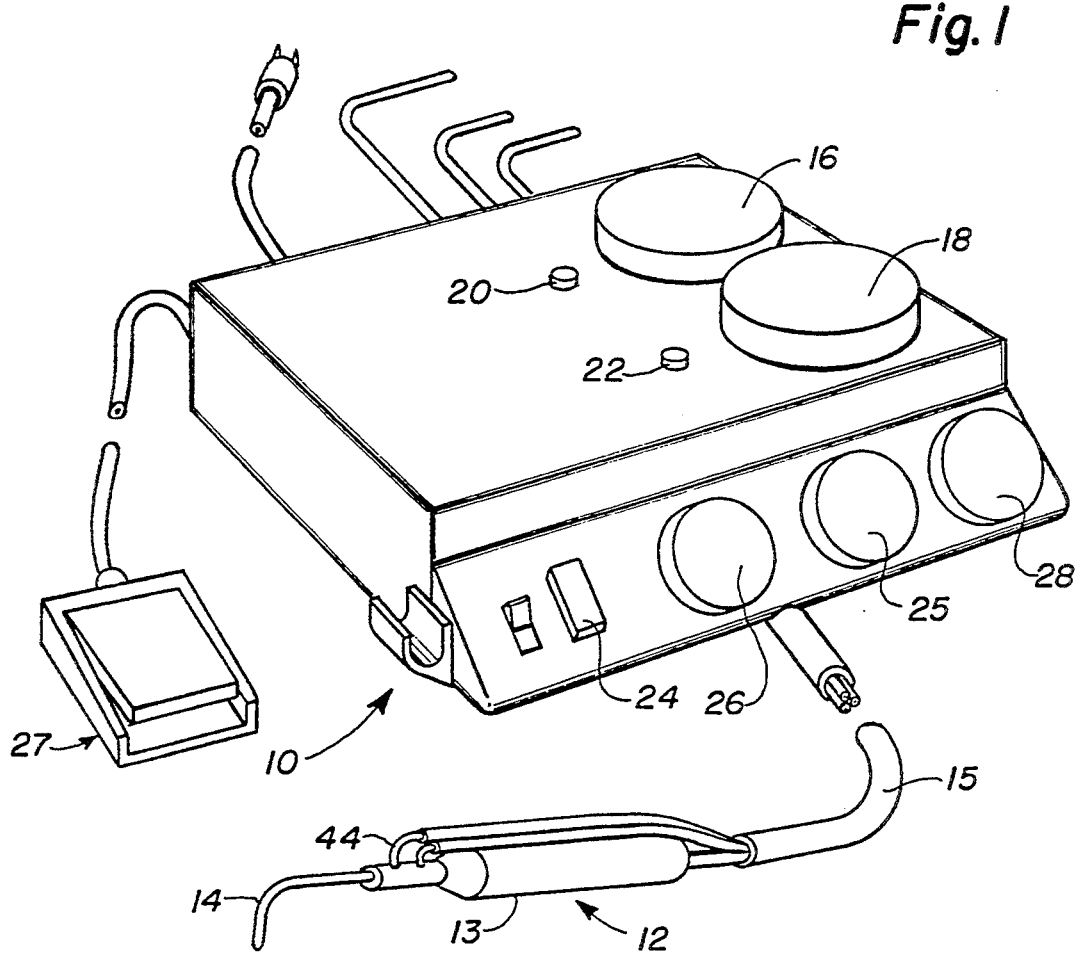
FIG. 1 is a perspective view of the apparatus of the invention including the base unit, foot switch and handpiece.

With reference now to FIGS. 1, 2, 3 and 5, the apparatus of the invention comprises a base unit 10, a handpiece 12 comprising handle 13 and insert 14 and foot switch 27. A conduit 15 connects the handpiece 12 to the base unit 10. Specifically, conduit 15 is connected to outlets 40 and 42 of separate cylindrical reservoirs 36 and 38, respectively, in base unit 10. Reservoirs 36 and 38 are provided to store one or more medicament fluids that can be transported from the reservoirs to be dispensed through handpiece 12 and insert 14 when desired. Fluid can be introduced into reservoirs 36 and 38 through a refill opening therein which are closed by caps 16 and 18 respectively.

In the illustrated embodiment, handle 13 has means therein which is adapted to impart a vibration to insert 14. Such means are well known in the art and may be mechanical, magnetostrictive or piezoelectric in nature. As is known in the art, when the tip 32 of insert 14 is touched lightly against a tooth by the practitioner, tip 32 is capable, because of its vibratory movement, of removing plaque and calculus from the tooth.

As is known to those skilled in the art, scaling tips adapted to vibrate anywhere from 6 to 50 KHZ may be used for scaling of teeth. In the illustrated embodiment, power control 26 may be used to vary the power of handle 13. Frequencies above about 20 KHZ are generally considered to be in the ultrasonic range.

Scaling below the gum line is known in the art as "root planing". As used herein, "scaling" is intended to embrace both the scaling of teeth and root planing.

The apparatus of the invention may be used as a conventional ultrasonic scaler, in which case switch 24 will be set to a first position (condition 1) so that no medicaments are delivered from reservoirs 36 and 38, and ordinary tap water is used to cool the scaling tip and to irrigate the mouth during ultrasonic scaling. Conventional ultrasonic inserts of the magnetostrictive type have a flow through passage that utilizes the water used to cool the transducer stack to also cool the scaling tip. The flow of the cooling water is conventionally set at about 35 cc/min and can be further controlled using flow control knob 25, and flow of cooling water to the handpiece is activated by setting foot control 27 to its second position. When foot control 27 is in the second position, solenoid valve 68 is activated permitting the flow of water through regulator 70, through solenoid 68 to handpiece 12 and over the scaling tip. When foot switch 27 is pushed to its second position, vibration of insert 14 is also initiated.

Vibration module 11 supplies the vibrating frequency to the handpiece by generating an oscillating electric current. In the illustrated embodiment the frequency of the electric current generated by vibration module 11 is directly related to the frequency at which the insert vibrates.

When switch 24 is set to a second position (condition 2) the apparatus is adapted for lavage by activating solenoids 56 and 58 which are put into operation by depressing one or both of buttons 20 and 22 and moving foot control 27 to its first position. When the apparatus is in this condition, air pressure from air supply 60 is reduced by regulator 66 forcing fluid from either reservoir 36 or 38 or both into conduit 15, through inlet 44 to insert 14 and through scaling tip 32 to be dispensed in the mouth. In the preferred embodiment the air pressure will be controlled by regulator 66, and the air supply will be maintained adjustably by control knob 28 at about 2–16 psi.

As is conventional in the art, the air supply line will be equipped with at least one filter 62, an inlet solenoid valve 64 and a regulator 66.

Those skilled in the art will recognize that in an alternative embodiment reservoirs 36 and 38, or the lines leading therefrom can be equipped with pump means for dispensing fluid from reservoirs 36 and 38.

It is also preferred that the lines leading from reservoirs 36 and 38 be equipped with check valves 61 and 71 which are used to insure that flow in the line is only in one direction. This prevents, for example, the flow of fluid from reservoir 38 to reservoir 36 when dispensing fluid from only reservoir 38. Vibration in insert 14 is initiated when footswitch 27 is moved to its second position.

By controlling the air pressure in the line as described above, flow control 28 is used to control the flow rate of fluid from reservoirs 36 and 38.

Circuitry may be provided which prevents activation of the vibration in the handpiece unless one or both of buttons 20 and 22 are depressed. This ensures that cooling fluid will always be available to tip 32 when insert 14 is vibrating.

In a preferred embodiment, especially for treating patients with gingivitis and periodontal disease, the practitioner may depress button 20, which will deliver a particular medicament to the handpiece from reservoir 36 through outlet 40; or he may depress button 22, which will deliver another medicament from reservoir 38 through outlet 42; or he may depress both buttons 20 and 22 to deliver a predetermined ratio of the medicaments from reservoirs 36 and 38 to handpiece 12.

In a preferred embodiment employing a handpiece using magnetostrictive elements, outlets 40 and 42 will connect within base unit 10 so that only one tube is needed to connect base unit 10 to handpiece 12 through inlet 44. Those skilled in the art, however, will recognize that, for some applications it may be more suitable to employ two or more conduits to connect base unit 10 to handpiece 12 so that the fluids from reservoirs 36 and 38 will combine in the handpiece, just before they are dispensed through insert 14. Using such an arrangement reduces the amount of flush time needed to clean the line when switching from one fluid reservoir to another. Besides the tube for medicaments connecting base unit 10 to handpiece 12, conduit 15 may contain one tube to carry cooling water to the transducer stack 30 and one tube to return cooling water from the handpiece 12 through outlet 46 to a sink or other depository, and the electrical wires needed to control the handpiece.

In an alternative embodiment, those skilled in the art will recognize that measured amounts of lavage irrigants, especially disinfecting fluids, may be used to first cool a transducer stack and be delivered through insert 14 to the area of operation.

As used herein, the term medicament includes antibacterial solutions adapted to fight bacteria associated with periodontal disease or dental caries, solutions adapted to increase resistance to dental caries such as fluoride solutions, surfactants adapted to chemically clean the sulcus and teeth of calculus, plaque and endotoxins, as well as chemical solutions containing chemicals to promote healing.

In the preferred embodiment scaler tip 32 will be made of stainless steel, will be tapered and will have dimensions suitable for entry into a periodontal pocket and will have roughly the dimensions of a periodontal probe. Accordingly, the scaling tip of the invention will have a diameter at distal end of tip 37, for example, of about 0.3–0.9 mm, preferably about 0.5–0.7 mm. The tip will be tapered so that the diameter of the tip at a point about 4 mm above the distal end will be about 0.05–0.7, preferably 0.05–0.3 mm greater than the diameter of the distal end of said tip. In the illustrated embodiment scaler tip 32 at end 37 is about 0.6 mm in diameter with a concentric oral delivery orifice 34 of about 0.25 mm, and a diameter of about 0.8 mm 4 mm above the distal end.

The amplitude of the insert 14 in ultrasonic operation will depend on the particular geometry of the particular insert used as well as the power output of the handpiece. The stroke amplitude can be therefore controlled by power control 26 to maintain clinical effectiveness and increase patient comfort when used subgingivally.

Figure 3:
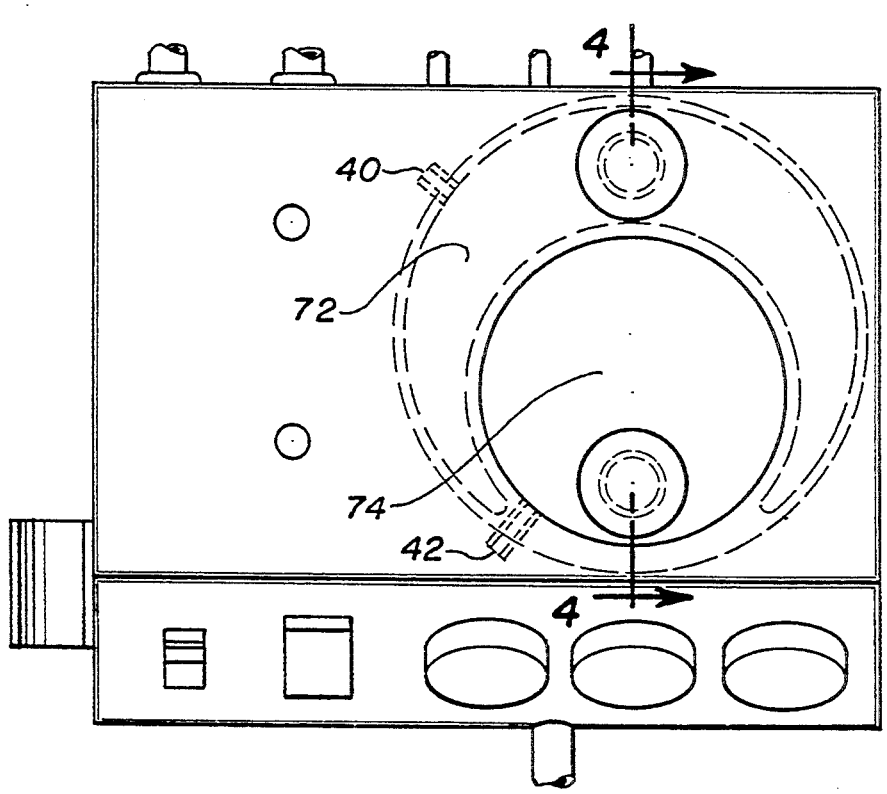
FIG. 3 is a cutaway top view of the base unit of the invention illustrating an alternative embodiment of the reservoir configuration.
Figure 2:
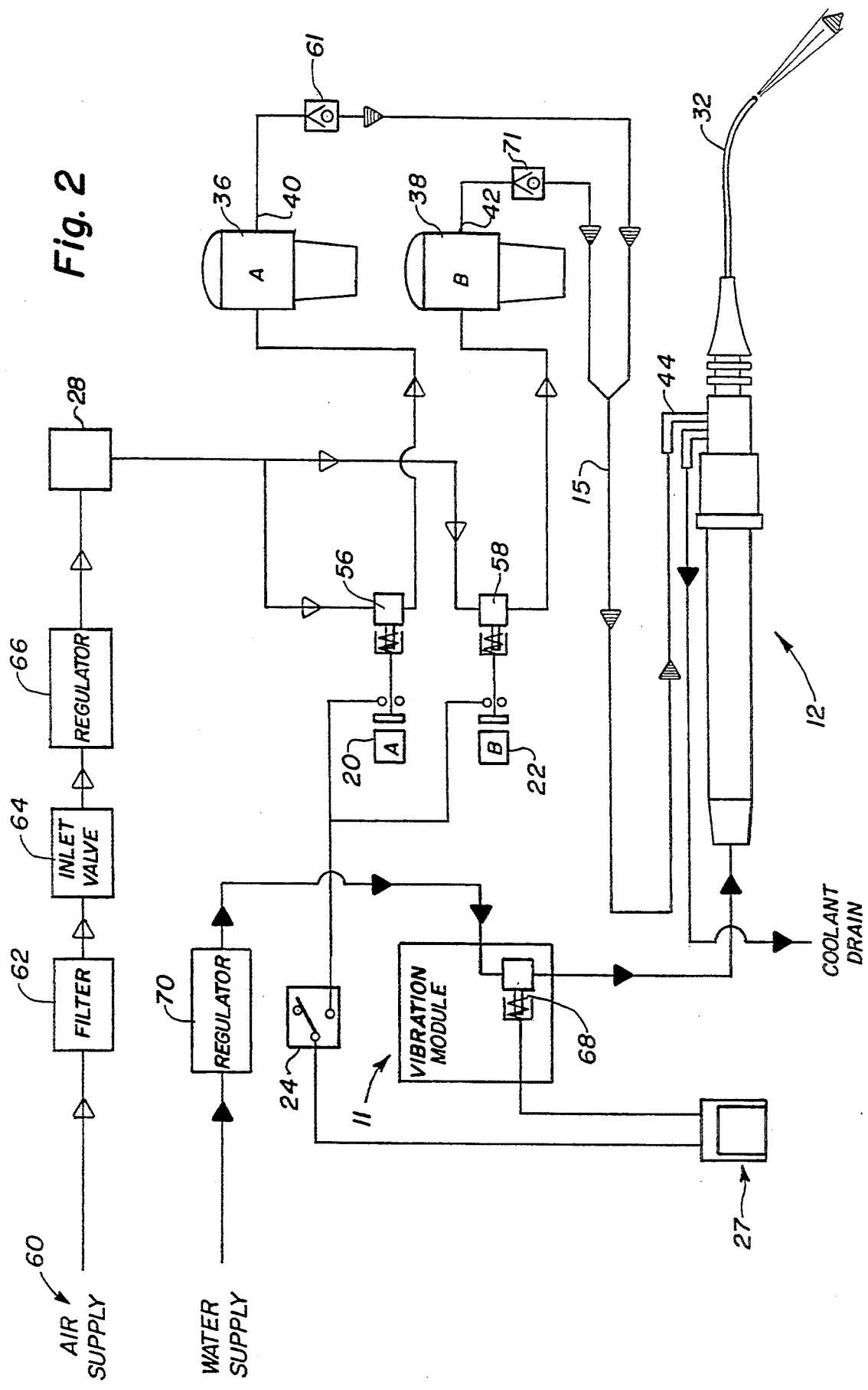
FIG. 2 is a schematic illustration of the apparatus of the invention.
Figure 4:
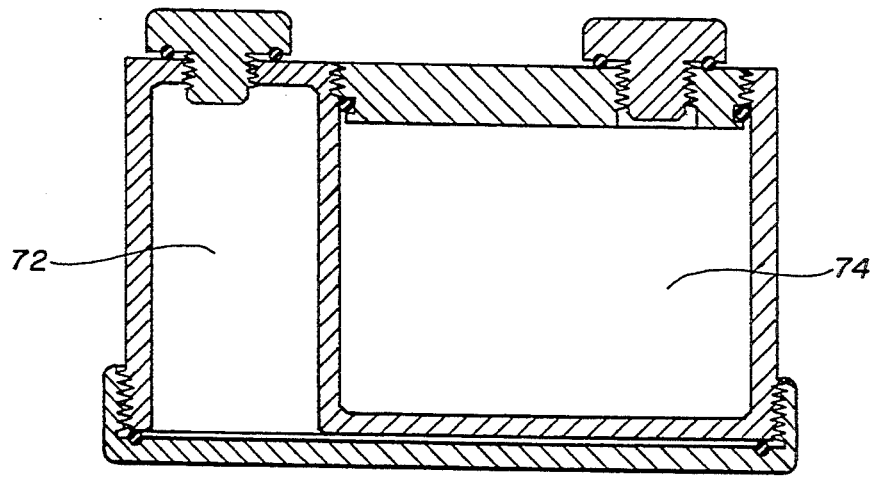
FIG. 4 is a cutaway side view along line 4—4 illustrating an alternative embodiment of the reservoir configuration of FIG. 3.

With reference now to FIGS. 3 and 4, in an alternative embodiment of base unit 10, reservoirs 72 and 74 may be contained within a single cylinder where reservoir 72 surrounds reservoir 74. Such a configuration utilizes available space efficiently and such a configuration may be desirable in an embodiment where larger reservoirs, up to about 1000 ml, are used.

Figure 5:
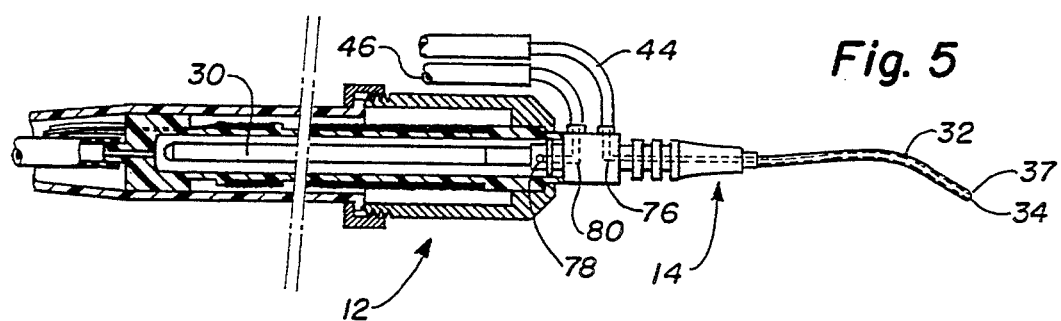
FIG. 5 is a cutaway view of a handpiece of the invention with a hollow tip and external flow return.

With reference now to FIG. 5 in the preferred embodiment, irrigant will be delivered through the scaler tip 32 through orifice 34 in apex or end 37 of scaler tip 32. Handpiece 12, having an insert 14, has an insert tip 32 with dimensions suitable for use in a periodontal pocket when the apparatus is operated in condition 2. Irrigant, preferably a medicament from reservoir 36 or 38, or both, enters insert 14 through inlet tube 44, travels through passage 76 and is dispensed through orifice 34. Hole 78 in insert 14 permits cooling water that passes over stack 30 to enter passage 80 to be conveyed through outlet 46 to be dispensed in the sink or other depository. An insert tip 32 with an apical orifice 34 is particularly suited for lavage of a periodontal pocket. When irrigant is dispensed from tip 32 while it is vibrating, the irrigant may be dispensed in a fine spray which helps clear the working area of debris. When used subgingivally in a periodontal pocket, this embodiment assures good irrigation of the pocket and debridment of plaque and calculus.

Figure 6:
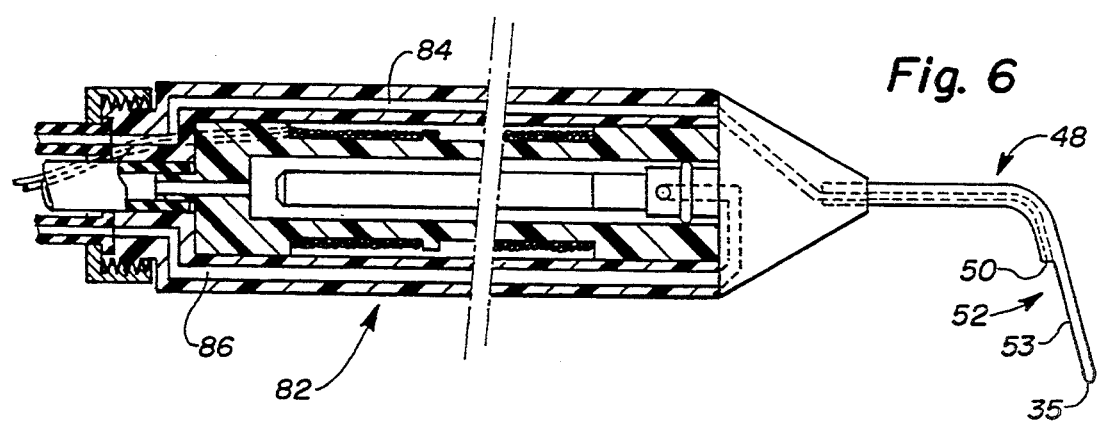
FIG. 6 is a alternative ultrasonic scaling, periodontal lavage handpiece.

With reference now to FIG. 6, an alternative handpiece 82 having an irrigant delivery tube 84 and a flow return tube 86 contained within the handpiece is illustrated. Handpiece 82 operates in the same manner as described for handpiece 12 in FIG. 5, but does not have the extraneous external tubing. Insert tip 48 is designed having a spray outlet 50 above the apex 35 and cutaway side 52 providing an external channel 53 on insert tip 48. Such an insert may be used to provide, for some applications, an alternative spray geometry in the treatment.

It will be recognized by those skilled in the art that an insert having a cutaway insert tip 48 may be used as part of a handpiece 12 and an insert tip 32 may be used as part of a handpiece 82, in addition to other combinations, as FIGS. 1–15 are illustrative only and are not limiting.

Figure 7:
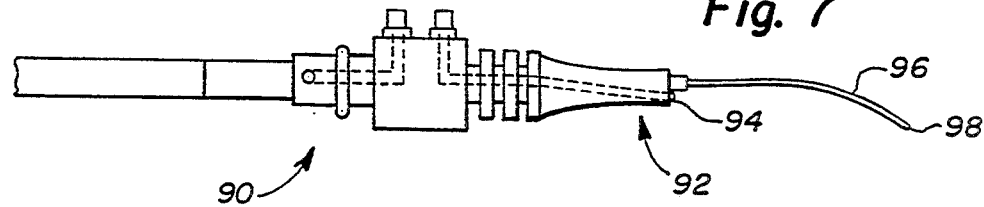
FIG. 7 is an alternative embodiment of a handpiece with means separate from the tip for spraying and cooling the tip.

With reference now to FIG. 7, in another alternative embodiment, insert 90 may have an end 92 having an outlet 94 for dispensing cooling or medicament fluid onto insert tip 96 which has an external channel for directing the fluid to apex 98 of the tip. In this embodiment, since the cooling fluid is external to tip 96, tip 96 may be made of a solid piece of metal. Such an embodiment permits further reduction in the size of the tip and may provide a longer lasting tip.

Reference is made now to FIGS. 8 and 9, which illustrate a preferred embodiment of the insert of the invention which can be used for ultrasonic scaling of teeth, root planing, and/or lavage. As in conventional ultrasonic inserts, insert 14 has as its main parts stack 30, connecting body 112, tip 32a and retaining means 115, which comprises tip guard 114 and retainer body assembly 116. Tip 32a, connecting body 112 and stack 30 comprise insert element 110. As is conventional in the art, stack 30 is integrally connected to connecting body 112 and tip 32a is integrally connected to connecting body 112 when tip 32a is brazed to connecting body 112 at braze 120. As used herein, in a fully assembled insert, scaling tip 32 will be defined to include tip 32a, or another described tip, and that portion of connecting body 112 that extends from nodal point 144 to braze 120, or a similar connecting point.

Shoulder 118 provides abutment against the handle 13 (FIG. 1) when insert 14 is assembled into handpiece 12. O-ring 126 provides a seal between the bore of handle 13 and insert 14 to prevent leakage of cooling liquid which passes over stack 30. Nodal point 144 represents the center point or zero point in the axial vibrational motion of insert 14. Insert 14 is relatively stationary at nodal point 144.

Those skilled in the art will recognize that o-rings 128 and 130 are in areas of low amplitude vibration. Accordingly, it is desirable that o-rings 128 and 130 are adapted to provide a seal when the insert is assembled.

In a handpiece using a conventional insert, the stack cooling liquid is used to also cool scaling tip 32. In the present invention, when cooling liquid passes into gap 122 its progress over connecting body 112 is stopped by O-ring 128 and the cooling liquid is forced to exit insert 14 through outlet 46. Fluids that are used to cool scaling tip 32 and irrigate the sulcus during operation enter the insert through inlet 44 into cross hole 124 and through bore 132 to orifice 34 of tip 32a. O-ring 130 prevents fluid from leaking over the outside of scaling tip 32.

Retainer pin 136 is provided to prevent scaling element 110 from moving axially or radially. Since retainer pin 136 provides a connection between insert element 110 and retaining means 115, a minimal vibration is transferred through pin 136 from element 110 to retaining means 115. Conversely, retaining means 115 damps the vibration of insert element 110 slightly.

Those skilled in the art will recognize that when it is desirable to do so, pin 136 may be loose fitting so that insert element 110 slides on pin 136 and the amount of vibration transferred from element 110 to retaining means 115 is minimized.

In a preferred embodiment of tip 32a, as illustrated in FIG. 10, the tip will be bent to facilitate access to hard to reach areas of the mouth. It has been found that the use of scaling tip 32 is best facilitated when it (as represented by central axis 146 of end 37) is at an angle of about 110°–118°, preferably about 114°, with (as represented by central axis 148) projection 138 of tip 32a. Projection 138 is provided for insertion into connecting body 112, having undercut 137 to enhance the brazing between connecting body 112 and tip 32a.

In a preferred embodiment the about 114° angle of the bend will be obtained utilizing two small bends 134 and 135. Using two bends substantially increases access of tip 32a to working areas of the mouth. Tip 32a preferably will have a length, from orifice 34 to the end of the radius of the second bend 135 of about 15–21 mm and a working tip at end 37 having a length of about 5–8 mm from orifice 34 to the beginning of the radius of first bend 134.

In a preferred embodiment it is desirable to further reduce the diameter of end 37, and simultaneously increase the wall thickness of end 37 of tip 32a by rotary swaging end 37. This work hardens and thereby increases the strength of scaling tip 32 at its point of contact in operation, and its reduced size further improves the access of scaling tip 32 into periodontal pockets.

Those skilled in the art will recognize that in some embodiments it may be desirable to reduce the size of tip 37 of scaling tip 32 by machining.

Referring now to FIG. 11 and 12, an embodiment of an insert 14a with a tip design adapted to direct irrigant on the outside of a scaling tip is illustrated. The configuration of the tip design of FIG. 11 is similar to that illustrated by Perdreaux in U.S. Pat. No. Re 30,536. The embodiment of FIG. 11 is similar to the embodiment of FIG. 8, the main differences being that there is no "O"-ring 130 and there is no bore 132 in scaling tip 32b or connecting body 112a so that fluid entering inlet 44 exits the insert through tip guard 114a around tip 32b. Tip guard 114a has tapered end 140 which provides a close fit around tip 32b. Although fluid surrounds tip 32b as it exits tip guard 114a, tip 32b has slot 142 which directs a greater portion of the fluid to the inside radius of bend 134 of tip 32b. The fluid that exits slot 142 is therefore channeled over the inside curvature of the tip toward end 37 thereof so that a significant portion of fluid is directed toward the area of interest in the scaling or lavage operation.

Referring now to FIG. 13, tip 32c is particularly adapted, using a single gooseneck bend 150, for scaling in deep periodontal pockets. Gooseneck bend 150 provides an angle of about 125°–145°, preferably about 135°, between tip end 37 (as represented by central axis 152) and projection 156 (as represented by central axis 154). Accordingly, the distance between the distal end of end 37 and the beginning of the radius of bend 150 is about 6–12 mm, preferably about 9 mm, and the distance between the distal end of end 37 and the end of the radius of bend 150 is about 17–23 mm.

Tip 32c may be adapted to be quickly removed or attached to connecting body 112b. For example, a quick connect device may be employed, such as a snap connection or a collet with a compressible ring, to quickly attach tip 32c to connecting body 112b. In the illustrated embodiment, threads 156 on projection 154 are used to provide the connection between tip 32c and connecting body 112b. Accordingly, tip 32c may be made to be disposable.

Those skilled in the art will recognize that modifications may be made that will make possible the utilization of tip 32c with insert 14, and tip 32a with insert 14a. The figures are illustrative only and are not limiting as to the various combinations of the use of the tips described with the various inserts described.

Those skilled in the art will recognize that a functional tip may be provided having different lengths and different working angles.

Those skilled in the art will recognize that all connectors and tubing used in the base unit, the conduit and the handpiece will be inert to the medicaments and irrigants used in the apparatus. In the preferred embodiment, the tubing and all connectors will be molded or extruded thermoplastic material.

With reference to FIG. 14 and 15, a tip 32d is provided with a right hand bend 162 which is suitable for root planing molars on the left side of the mouth.

Those skilled in the art will recognize that a similar tip may be provided, with the opposite bend, for root planing on the right side of the mouth.

Tip 32d is also adapted for end delivery through bore 132 through an orifice 34. Tip 32d has a gooseneck type bend 150a in addition to bend 162 and may be made similar to the tip illustrated in FIG. 10 except that bend 162 will be made in a different plane from bend 150a instead of substantially the same plane (as illustrated by bends 134 and 135 of FIG. 10).

The medicaments dispensed from reservoirs 36 and 38 may be chosen to specifically effect a particular treatment. For example, hydrogen peroxide or a chlorohexidine solution may be chosen for the treatment of periodontal disease; zinc chloride solution, cetylpyridinium chloride solution, or a stannous fluoride solution may be chosen to treat plaque, or for treatment of dental caries; or a surfactant solution may be used for chemically removing endotoxins from the surface of the teeth and gums. Since buttons 20 and 22 may be depressed to permit flow from reservoirs 36 and 38 to occur simultaneously, the practitioner has the capability of providing treatment for periodontal disease and plaque simultaneously. As is known to those skilled in the art, some of the medicaments which are desirable for use in such treatments are short-lived and cannot be stored in a condition ready for use. Accordingly, using reservoirs 36 and 38 to store the components of short-lived medicaments makes it possible to form the desired medicaments in situ by delivering the two components from reservoirs 36 and 38 simultaneously to form the desired, short-lived medicament in the mouth or the handpiece or the conduit leading to the handpiece.

The medicaments distributed from reservoirs 36 and 38 may be any of those known to those skilled in the art to be effective in the treatment of periodontal disease. In the preferred embodiment the irrigants will be selected from the group comprising solutions containing sodium hypochlorite, hydrogen peroxide, zinc chloride with or without sodium fluoride, quaternary compounds including cetylpyridinium chloride, stannous fluoride, chlorine dioxide, sodium bicarbonate, chorohexidine (for example chlorhexidine gluconate) and mixtures thereof.

Irrigant is dispensed through the scaler tip 32 or 48 in sufficient volume to remain constantly available to infected sites. The flow rate desired will depend on the patient and the particular treatment desired. The flow rate of irrigant will be about 3–20 ml/min and most preferably 5–10 ml/min. The flow rate for a particular treatment may be controlled by flow rate control knob 28. The capacity of reservoirs 36 and 38 will be such that irrigant storage is sufficient for about 5 minutes to 5 hours, and preferably at least 10–20 minutes of continuous use. Accordingly, the capacity of each reservoir may be from about 100 to 1000 ml and more as desired.

In its operation, when switch 24 is in the condition 2 position, the apparatus will be adapted for scaling while dispensing medicament from one or both of reservoirs 36 and 38. When button 22 is depressed, medicament will be distributed from reservoir 38 through outlet 42 and into conduit 15. The medicament will flow through conduit 15 to handpiece 12, through inlet 44 to insert 14. The medicament will flow through insert tip 32 and will be dispersed through orifice 34 at the end 37 of tip 32.

Tip 32 has a shape and size, and has a tapered end 37 at orifice 34 such that it will fit into a periodontal pocket. End 37 has a shape and strength suitable for scaling of teeth.

Optionally, for the comfort of the patient, the apparatus may be provided with a small heater in handpiece 12 or in conduit 15 to aid in heating the irrigant dispensed in the mouth to about 35°–38° C.

Since its flow through the apparatus and its flow through the scaling tip may cause medicament solutions to foam, as will be appreciated by those skilled in the art, it may be desirable to add antifoaming agents to the medicament solution to reduce the foaming.

For the convenience and comfort of the patient, it is desirable to add a flavor to the medicament solution.

In the preferred embodiment of the invention, the medicament fluid used as an irrigant will have antibacterial activity sufficient to substantially destroy airborne bacteria in the operatory.

Examples of medicament compositions that may be used as irrigants for scaling and periodontal lavage are illustrated in, for example, U.S. Patents

| | |
|---|---|
| 3,864,472 | 4,472,373 |
| 3,887,701 | 4,522,806 |
| 4,160,821 | 4,582,702 |
| 4,339,432 | 4,601,900 |

Those skilled in the art will be able to determine which compositions described therein will most beneficially be used in the apparatus of the invention.

Illustrated embodiments of fluid solutions that may be used in the apparatus of the invention follow.

In the following examples:

Hystar 5875 is hydrogenated starch hydrolysate available from LONZA.

Flavor is a spearmint oil/peppermint oil flavor available from Unter & Co.

SDA-38B, SDA-37B and SDA-36B are 200 proof alcohol.

| INGREDIENTS: | PERCENT: |
|---|---|
| *Example 1* | |
| Water Purified | 85.3275 |
| Hystar 5875 | 2.0000 |
| Sodium Saccharin | 0.0500 |
| Sodium Citrate | 0.1000 |
| Zinc Chloride | 0.1500 |
| Sodium Fluoride | 0.0200 |
| FD & C Green #3 | 0.0005 |
| FD & C Yellow #10 | 0.0020 |
| Tween 80 | 0.5000 |
| Flavor | 0.2500 |
| SDA-37B, ethanol | 11.6000 |
| | 100.0000 |
| *Example 2* | |
| Water Purified | 84.09425 |
| Hystar 5875 | 2.00000 |
| Spectradyne G (20% chlorohexidine solution) | 0.80000 |
| Sodium Saccharin | 0.00500 |
| D & C Yellow #10 | 0.00025 |
| D & C Yellow #6 | 0.00050 |
| Tween 80 | 1.0000 |
| Flavor | 0.5000 |
| SDA-38B, ethanol | 11.6000 |
| | 100.0000 |
| *Example 3* | |
| Water Purified | 77.45465 |
| Hystar 5875 | 2.00000 |
| Sodium Saccharin | 0.05000 |
| Benzoic Acid | 0.00010 |

| INGREDIENTS: | PERCENT: |
|---|---|
| *-continued* | |
| Cetylpyridinium Chloride | 0.04500 |
| FD & C Blue #1 | 0.00025 |
| Tween 80 | 1.0000 |
| Flavor | 0.5000 |
| SDA-36B, ethanol | 18.9500 |
| | 100.0000 |

While present embodiments of the invention and methods of practicing the same have been illustrated and described, it will be recognized by those skilled in the art that this invention may be otherwise variously embodied and practiced within the scope of the following claims.

What is claimed is:

1. A method for subgingival scaling and lavage, comprising the steps of:
   I. providing an insert having
     (a) a tip for scaling and delivery of lavage fluids, said tip having a distal end and a concentric oral delivery orifice, said concentric oral delivery orifice having a diameter of about 0.25 mm positioned at said distal end of said tip, said distal end of said tip having a diameter of from 0.3 mm to 0.9 mm,
     (b) retaining means for retaining said scaling tip in said insert
     (c) path means for delivering irrigant for scaling or for lavage through said insert and to said concentric oral delivery orifice at said distal end of said tip in which said path means comprises inlet means for permitting flow of fluid into said retaining means and a bore through said tip communicating with said inlet means, and
     (d) a magnetostrictive stack, and a connecting body attached to said stack and said tip attached to said connecting body wherein said tip is adapted for ultrasonic scaling below the gumline in periodontal pockets and said insert has outlet means for removing stack cooling water from around said stack in a direction away from said tip, subgingivally scaling and lavaging by subgingivally delivering from about 3 ml/min to about 20 ml/min of irrigant through said orifice to a dental tooth subgingival surface.

2. The method of claim 1 in which said tip is brazed to said connecting body.

3. The method of claim 1 in which said scaling tip is attached to said connecting body by quick connect means.

4. The method of claim 3 in which said tip is disposable.

5. The method of claim 1 in which said tip is connected to said connecting body by thread means.

6. The method of claim 1 in which the diameter of the distal end of said tip is reduced by rotary swaging.

7. The method of claim 1 in which the distal end of said tip has a diameter of about 0.5 to 0.7 mm.

8. The method of claim 7 in which the end of said tip is tapered so that the diameter of said tip at a point about 4 mm above said distal end will be about 0.05 to 0.5 mm greater than the diameter of the distal end of said tip, and a diameter about 8 mm above said distal end of about 0.1 to 1 mm greater than the diameter of said distal end.

9. The method of claim 1 in which the tip is shaped to provide easy access to difficult to reach places in the mouth wherein said shape provides an angle of about 109°-119° between the central axis of the distal end of said tip and the central axis of said connecting body.

10. The method of claim 9 in which said angle is about 114°.

11. The method of claim 10 in which said about 114° angle is obtained as the result of two bends in said scaling tip.

12. The method of claim 11 in which said two bends are of substantially equal radius.

13. The method of claim 1 in which the tip is shaped to provide easy access to difficult to reach places in the mouth wherein said shape provides an angle of about 125°-145° between the central axis of the distal end of said tip and the central axis of said connecting body.

14. The method of claim 13 in which said angle is about 135°.

15. The method of claim 1 in which said tip has two bends in substantially different planes and is adapted for subgingivally scaling bifurcated areas of molars while providing end delivery of irrigants.

16. The method of claim 1 in which said tip has a projection with an undercut adapted to enhance the braze between said tip and a connecting body.

17. The method of claim 1 in which said tip has a threaded projection adapted to provide a removable attachment between said tip and a connecting body.

18. The method of claim 17 in which said tip is disposable.

19. A method for using a tip with an insert for subgingival scaling and lavage comprising the steps of:
(a) providing means for detachably attaching said tip to a connecting body of said insert, said tip having a distal end and a concentric oral delivery orifice, said concentric oral delivery orifice positioned at said distal end of said tip, said distal end of said tip having a diameter of less than 0.9 mm and
(b) subgingivally scaling and lavaging a tooth by delivering irrigant to said tooth through an orifice having a diameter of about 0.25 mm at said distal end of said tip subgingivally scaling or lavaging by subgingivally delivering from about 3 ml/min to about 20 ml/min of irrigant through said orifice to a dental tooth.

20. The method of claim 19 in which said tip has a projection with an undercut adapted to enhance brazing between said tip and a connecting body.

21. The method of claim 19 in which said tip has quick connect means adapted to provide a removable attachment between said tip and a connecting body.

22. The method of claim 19 in which said tip is disposable.

23. The method of claim 19 in which the distal end of said tip has a diameter of about 0.5 to 0.7 mm.

24. A method of subgingival scaling comprising the steps of:
I. providing an insert housing having:
(a) a tip for scaling and delivery of lavage fluids, said tip having a distal end and a concentric oral delivery orifice, said concentric oral delivery orifice having a diameter of about 0.25 mm positioned at said distal end of said tip, said distal end of said tip having a diameter of from 0.3 mm to 0.9 mm,
(b) retaining means for retaining said scaling tip in said insert,
(c) path means for delivering irrigant for scaling or for lavage through said insert and to said concentric oral delivery orifice at said distal end of said tip in which said path means comprises inlet means for permitting flow of fluid into said retaining means and a bore through said tip communicating with said inlet means, and
(d) a magnetostrictive stack, and a connecting body attached to said stack and said tip attached to said connecting body wherein said tip is adapted for ultrasonic scaling below the gumline in periodontal pockets and said insert has outlet means for removing stack cooling water from around said stack in a direction away from said tip, and
II. scaling and lavaging teeth subgingivally using said tip, subgingivally delivering from about 3 ml/min to about 20 ml/min of irrigant through said orifice to a dental tooth.

25. A method of scaling and lavaging, comprising the steps of:
I. providing a tip having
(a) means for detachably attaching said tip to a connecting body of an insert, said tip having a distal end and a concentric oral delivery orifice, said concentric oral delivery orifice having a diameter of about 0.25 mm positioned at said distal end of said tip, said distal end of said tip having a diameter of less than 0.9 mm and
(b) path means for delivering irrigant for scaling or for lavage to said distal end of said tip, wherein said distal end of said tip is tapered so that the diameter of said tip at a point about 4 mm above said distal end is about 0.05 mm to 0.5 mm greater than the diameter of the distal end of said tip, and a diameter about 8 mm above said distal end of is about 0.1 mm to 1 mm greater than the diameter of said distal end, and scaling and lavaging teeth subgingivally using said tip and an irrigant comprising at least one medicament,
by subgingivally delivering from about 3 ml/min to about 20 ml/min of said irrigant through said orifice to a dental tooth subgingival surface.

26. The method of claim 25 wherein said distal end of said tip is about 0.6 mm in diameter.

* * * * *